US006051558A

United States Patent [19]
Burns et al.

[11] Patent Number: 6,051,558
[45] Date of Patent: Apr. 18, 2000

[54] COMPOSITIONS SUITABLE FOR CONTROLLED RELEASE OF THE HORMONE GNRH AND ITS ANALOGS

[75] Inventors: Patrick J. Burns, Lexington, Ky.; John W. Gibson, Springville; Arthur J. Tipton, Birmingham, both of Ala.

[73] Assignee: Southern BioSystems, Inc., Birmingham, Ala.

[21] Appl. No.: 09/001,123

[22] Filed: Dec. 30, 1997

Related U.S. Application Data

[60] Provisional application No. 60/047,789, May 28, 1997.

[51] Int. Cl.⁷ .................................................. A61K 38/00
[52] U.S. Cl. ............................ 514/15; 514/16; 424/499; 424/45; 424/423; 424/430; 424/435; 424/436; 443/451; 443/464
[58] Field of Search .......................... 514/15, 16; 424/45, 424/423, 430, 435, 436, 443, 451, 464, 499

[56] References Cited

U.S. PATENT DOCUMENTS

| | | | |
|---|---|---|---|
| 3,853,837 | 12/1974 | Fujino et al. | 260/112.5 |
| 3,992,365 | 11/1976 | Beddell et al. | 260/112.5 |
| 4,024,248 | 5/1977 | Konig et al. | 424/177 |
| 4,100,274 | 7/1978 | Dutta et al. | 424/177 |
| 4,411,890 | 10/1983 | Momany | 424/177 |
| 5,352,662 | 10/1994 | Brooks et al. | 514/12 |
| 5,391,381 | 2/1995 | Wong et al. | 424/473 |
| 5,399,363 | 3/1995 | Liversidge et al. | 424/490 |
| 5,487,898 | 1/1996 | Lu et al. | 424/435 |
| 5,545,408 | 8/1996 | Trigg et al. | 424/539 |
| 5,736,152 | 4/1998 | Dunn | 424/426 |
| 5,747,058 | 5/1998 | Tipton et al. | 424/423 |
| 5,750,100 | 5/1998 | Yamagata et al. | 428/85.2 |
| 5,840,329 | 11/1998 | Bai | 424/548 |

FOREIGN PATENT DOCUMENTS

| | | | |
|---|---|---|---|
| WO 91/18016 | 11/1991 | WIPO | C07K 7/20 |
| WO 93/07833 | 4/1993 | WIPO | A61D 19/00 |

OTHER PUBLICATIONS

Becker, S.E., et al. "Effects of Gonadotropin–Releasing Hormone Infused in a Pulsatile or Continuous Fashion on Serum Gonadotropin Concentrations and Ovulation in the Mare," *J. Anim. Sci.* (1992) 70:1208–1215.

Bühler, K., GnRH Agonists and Safety, In *GnRH Analagoues The State of the Art 1993*, A Summary of the 3rd Internaitonal Symposium on GnRH Analogues in Cancer and Human Reproduction, Geneva, Feb. 1993.

Fleury, J., et al. "Evaluation of the Saber™ Delivery System for the Controlled Release of the Deslorelin for Advancing Ovulation in the Mare: Effects of Formulation & Dose," *Proceed. Int'l Symp. Control. Rel. Bioact. Mater.* 25 (1998) Controlled Release Society, Inc. pp. 657–658.

Ginther, O.J., Reproductive Biology of the Mare: Basic and Applied Aspects, *EquiServices*, Chapter 12, 499–508 Cross Plains, Wisconsin (1970).

Ginther, O.J. et al. "Effect of a Synthetic Gonadotropin–Releasing Hormone on Plasma Concentrations of Luteinizing Hormone in Ponies," *Am. J. Vet. Res.*, 35: 79–81 (1974).

Ginther, O.J., "Ultrasonic Imaging and Reproductive Events in the Mare," *Equiservices*, Cross Plains, WI Chapter 4: 43–72 (1986).

Hyland, J.H., et al. "Infusion of Gonadotrophin–Releasing Hormone (GnRH) Induces of Ovulation and Fertile Oestrus in Mares During Seasonal Anoestrus," *J. Reprod. Fert.*, Suppl. 35 (1987), 211–220.

Irvine, C.H. G., "GnRH Clinical Application," In *Equine Reproduction*, (eds) McKinon, A.O. and Voss, J.L., Chapter 36, pp. 41–45, Lea & Febiger (1993).

Irvine, D.S., et al., "Duration of Oestrus and Time of Ovulation in Mares Treated with Synthetic GnRH (Ay24, 031)," *J. Reprod. Fert. Supp.* 23:279–283 (1975).

Jochle, W., et al., Control of Ovulation in the Mare with Ovuplant™, a Short–Term Release Implant (STI) Containing the GNRH Analogue Deslorelin Acetate: *J. Eq. Vet. Sci.*, 44:632 (1994).

LaCoste, D., et al., "Reversible Inhibition of Testicular Androgen Secretion by 3–, 5–and 6–Month Controlled–Release Microsphere Formulations of the LH–RH Agonist [D–Trp⁶, des–Gly–NH₂¹⁰] LH–RH Ethylamide in the Dog," *J. Steroid Biochem.* 33:5, 1007–1011 (1989).

Loy, R.G. et al. "The Effects of Human Chorionic Gonadotrophin on Ovulation, Length of Estrus, and Fertility in the Mare," *Cornell Vet.* 56:41–50 (1966).

McCarthy, P.F., et al., "Management of Stallions on Large Breeding Farms," Blanchard, T.K. and Varner, D.D. (eds.) Stallion Management, *Vet. Clin. N. Amer. Equine Prac.*, 8:219–236 (1992).

McKinnon, A.O., et al. "Effect of a GnRH Analogue (Ovuplant), hCG and Dexamethasone on Time to Ovulation in Cycling Mares," *World Equine Veterinary Review*, (1997) 2:3 16–18.

Mearns, D., "Sires' Live–Foal Percentages in 1996," *The Blood Horse*, vol. 39, 4794 (1996).

Merrifield, B., *Science* 232:342 (1986).

Montovan, S.M., et al., "The Effect of a Potent GnRH Agonist on Gonadal and Sexual Activity in the Horse," *Theriogenology*, 33:6, 1305–1321 (1990).

Nett et al., "Further Studies on the Radioimmunoassay of Gonadotropin–Releasing Hormone: Effect of Radioiodination, Antiserum and Unextracted Serum on Levels of Immunoreactivity in Serum," *Endocrinology* 101: 1135 (1977).

Rabb et al., "Effects of Active Immunication Against GnRH on LH, FSH and Prolactin Storage, Secretion and Response to Their Secretagogues in Pony Geldings," *J. Anim. Sci.*, 68: 3322–3329 (1990).

(List continued on next page.)

*Primary Examiner*—F. T. Moezie
*Attorney, Agent, or Firm*—Bruce D. Gray, Esq.; Kilpatrick Stockton LLP

[57] ABSTRACT

A liquid composition for the controlled release of gonodotropin releasing hormone (GnRH) or its analogs is provided that includes: (i) a non-polymeric, non-water soluble liquid carrier material (HVLCM) of viscosity of at least 5,000 cP at 37° C. that does not crystallize neat under ambient or physiological conditions; and (ii) GnRH or analogs thereof.

20 Claims, 1 Drawing Sheet

OTHER PUBLICATIONS

Roser, J.J., et al., "The Development of Antibodies to Human Chorionic Gonadotropins Following its Repeated Injection in the Cyclic Mare," *J. Reprod. Fert. Suppl.*, 173–179 (1979).

Sullivan, J., "Duration of Estrus and Ovulation Time in Nonlactating Mares Given Human Chorionic Gonadotropin During Three Successive Estrous Periods," *J. Am. Vet. Med. Assoc.*, 63:895 (1973).

Thompson, Jr., D.L., et al., "Effects of Melatonin and Thyrotropin Releasing Hormone of Mares During the Nonbreeding Season," *J. Anim. Sci.*, 58:3, 668–677(1983).

Thompson, Jr., D.L., et al., "Testosterone Effects on Mares During Synchoronization with Altrenogest: FSH, LH, Estrous, Duration and Pregnancy Rate," *J. Anim. Sci.*, 56: 3, 678–686 (1983).

Voss, J.L., et al. "The Effect of HCG on Duration of Oestrus, Time and Fertility in Mares," *J. Reprod. Fert.*, Suppl. 23 (1975) 297–301.-

COMPOSITIONS SUITABLE FOR CONTROLLED RELEASE OF THE HORMONE GNRH AND ITS ANALOGS

This application claims priority to U.S. Provisional Application No. 60/047,789 filed on May 28, 1997 now abandoned.

BACKGROUND OF THE INVENTION

In the horse industry development of an accurate, economical method for the precise control of ovulation in the mare would greatly benefit reproductive management of mares and stallions. The mares' extended estrus period, with ovulation at any time from 1 to 10 days after the beginning of estrus, has made reproductive management of mares time-consuming, expensive and most importantly, inefficient. In the mare, GnRH or its analogs are beginning to be used as alternative non-antigenic substitutes to replace hCG to hasten ovulation in preovulatory mares. This is because repeated use of hCG has been associated with decreased response [Sullivan, J., J Am. Vet. Med. Assoc. 63:895 (1973)] and anti-hCG antibody formation [Roser, J., J. Reprod. Fert. Suppl. 173–179(1974)]. Current data suggest that ovulation induction with potent GnRH analogs requires multiple injections of very low doses [Harrison, L., et al., J. Eq. Vet Sci. 11:163–166(1991)] or a very high dose given as a slow releasing implant [Jochle, W. et al., J. Eq. Vet. Sci. 44:632(1994)].

The selection of an appropriate drug delivery system should be based on the pharmacokinetic and pharmacodynamic properties of the drug. The importance of the pharmacodynamic properties of a drug is especially relevant in the case of hormones that target specific high affinity receptors to produce their effect. In the case of GnRH this relationship is dependent on multiple elements including species, reproductive status and complex concentration/presentation effects of the peptide and pituitary responsiveness to it.

Applicants have discovered that certain compositions are suitable for controlled release of GnRH analogs, particularly for the purpose of advancing ovulation in mares. The composition includes a system based on sucrose acetate isobutyrate (SAIB) a fully-esterified sucrose molecule. SAIB is a low molecular wt material that has many of properties associated with polymeric materials. Because SAIB is a non-polymer, dilution with only small amounts of solvents are required to give an easily-injectable solution.

BRIEF DESCRIPTION OF THE INVENTION

Applicants have discovered a particular adaptation of the SAIB drug delivery system technology suitable for inducing ovulation in mares, with a composition that is both injectable and sterilizable.

ABBREVIATION AND DEFINITIONS

| | |
|---|---|
| GnRH | Gonodotropin releasing hormone, also known as LH-RH or LHRH |
| HVLCM | High viscosity liquid carrier material |
| LH | Luteinizing Hormone |
| LH-RH | Luteinizing Hormone-releasing Hormone |
| LVLCM | Low viscosity liquid carrier material |

DETAILED DESCRIPTION OF THE INVENTION

Figure 1:
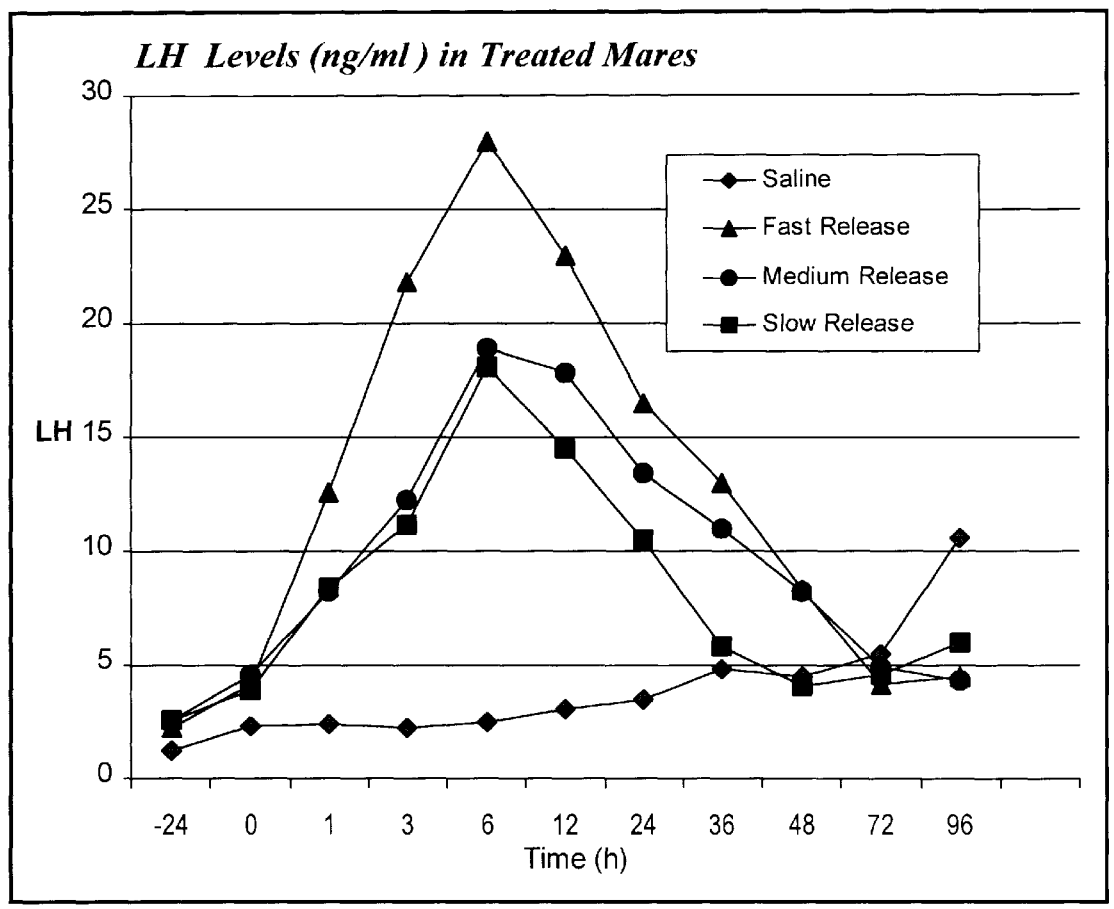
FIG. 1 shows LH concentrations in mares following treatment with experimental formulations.

The present invention relates to a composition for the controlled release of GnRH or analogs thereof in mares to induce ovulation, comprising:
  (a) a non-polymeric, non-water soluble liquid carrier material having a viscosity of at least 5,000 cP at 37° C. that does not crystallize neat under ambient or physiological conditions;
  (b) GnRH or analogs, or combination thereof.

In one embodiment of the composition of the present invention, the non-water soluble liquid carrier material is sucrose acetate isobutyrate.

In another embodiment of the composition of the present invention, the non-water soluble liquid carrier material is present in an amount from about 99.5 percent to about 10 percent by weight, relative to the total weight of the composition.

In another embodiment of the composition of the present invention, the non-water soluble liquid carrier material is present in an amount from about 95 percent to about 25 percent by weight, relative to the total weight of the composition.

In another embodiment of the composition of the present invention, the composition further comprises a solvent in which the non-water soluble liquid carrier is soluble.

In another embodiment of the composition of the present invention, the solvent is selected from the group consisting of ethanol, dimethylsulfoxide, ethyl lactate, ethyl acetate, benzyl alcohol, triacetin, N-methylpyrrolidone, propylene carbonate, and glycofurol.

In another embodiment of the composition of the present invention, the solvent is ethanol.

In another embodiment of the composition of the present invention, the solvent is present in an amount from about 10 to about 50 percent by weight, relative to the weight of the composition.

In another embodiment of the composition of the present invention, the analog is deslorelin.

In another embodiment of the composition of the present invention, the analog is selected from deslorelin, avorelin, leuprolide, and natural LHRH.

The present invention also relates to a liquid composition for the controlled release of GnRH or analogs thereof in mares to induce ovulation, comprising sucrose acetate isobutyrate and ethanol in a weight ratio of between about 75:25 and about 60:40, and GnRH or analog thereof or combination thereof in a concentration of between about 0.1 to about 5.0 mg/ml of liquid composition, to provide a dose of between about 0.3 mg and about 10 mg of GnRH or analog thereof or combination thereof.

The present invention also relates to a liquid composition for the controlled release of GnRH or analogs thereof in mares to induce ovulation, comprising sucrose acetate isobutyrate and ethanol in a weight ratio of between about 75:25 and about 60:40, and GnRH or analog thereof or combination thereof in a concentration of between about 1.0 to about 2.5 mg/ml of liquid composition, to deliver a dose of between about 0.3 mg and about 10 mg of GnRH or analog thereof or combination thereof.

In one embodiment of the liquid compositions of the present invention, the analog of GnRH is Deslorelin.

In another embodiment of the liquid compositions of the present invention, the composition is sterilized before administration to mares.

In another embodiment of the liquid compositions of the present invention, composition is filter sterilized before administration to mares.

The present invention also relates to a filter sterilized liquid composition for the controlled release of Deslorelin in mares to induce ovulation, comprising sucrose acetate isobutyrate and ethanol in a weight to weight ratio of about 75:25, and Deslorelin at a concentration of between about 0.1 and about 5.0 mg/ml of liquid composition, to deliver a dose between about 1 mg and about 2 mg of deslorelin, said composition administrable by injection.

The present invention also relates to a filter sterilized liquid composition for the controlled release of Deslorelin in mares to induce ovulation, comprising sucrose acetate isobutyrate and ethanol in a weight to weight ratio of about 75:25, and Deslorelin at a concentration of between about 1.0 and about 2.5 mg/ml of liquid composition, to deliver a dose between about 1 mg and about 2 mg of deslorelin, said composition administrable by injection. ps I. High Viscosity Liquid Carrier Material (HVLCM)

A high viscosity liquid carrier material should be selected that is non-polymeric, non-water soluble, and has a viscosity of at least 5,000 cP, (and optionally at least 10,000, 15,000; 20,000; 25,000 or even 50,000 cP) at 37° C., and that does not crystallize neat under ambient or physiological conditions. The term non-water soluble refers to a material that is soluble in water to a degree of less than one percent by weight under ambient conditions.

In a preferred embodiment, the HVLCM significantly decreases in viscosity when mixed with a solvent to form a LVLCM that can be mixed with a substrate for controlled delivery. The LVLCM/substrate composition is typically easier to place in the body than a HVLCM/substrate composition, because it flows more easily into and out of syringes or other implantation means, and can easily be formulated as an emulsion. The LVLCM can have any desired viscosity. It has been found that a viscosity range for the LVLCM of less than approximately 1000 cP, and more particularly less than 200 cP, is typically useful for in vivo applications.

In a preferred embodiment, sucrose acetate isobutyrate ("SAIB"), a sucrose molecule esterified with two acetic acid and six isobutyric acid moieties, is used as the HVLCM. The structure of SAIB is set forth below.

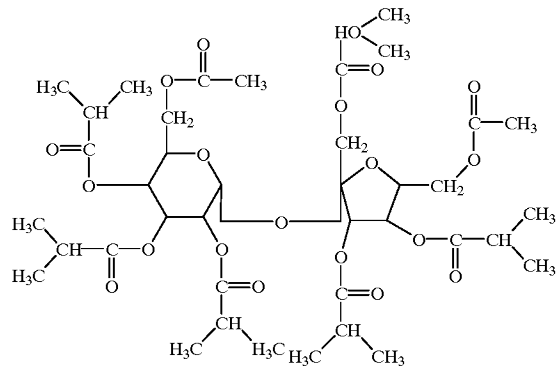

SAIB is orally non-toxic and is currently used to stabilize emulsions in the food industry. It is a very viscous liquid and has an unusual property that there is a dramatic change in viscosity with small additions of heat or with the addition of solvents. It is soluble in a large number of biocompatible solvents. When in solution or in an emulsion, SAIB can be applied via injection.

In other embodiments, the HVLCM can be stearate esters such as those of propylene glycol, glyceryl, diethylaminoethyl, and glycol, stearate amides and other long-chain fatty acid amides, such as N,N'-ethylene distearamide, stearamide MEA and DEA, ethylene bistearamide, cocoamine oxide, long-chain fatty alcohols, such as cetyl alcohol and stearyl alcohol, long-chain esters such as myristyl myristate, beheny erucate, and glyceryl phosphates. In a particular embodiment, the HVLCM is acetylated sucrose distearate (Crodesta A-10).

The HVLCM is present in the composition in any amount that achieves the desired affect. The HVLCM is typically present in controlled delivery compositions for GnRH or its analogs in an amount in the range from about 99.5 percent to about 10 percent by weight, more typically, between about 90 and about 25 percent, and most typically, between about 85 and about 65 percent, relative to the total weight of the composition.

II. Substance to be Delivered

A variety of analogs of gonodotrophlin releasing hormone are suitable for controlled release in the compositions of the present invention. Suitable analogs include, but are not limited to those listed in the following Table I.

TABLE I

| Agonist structure | Name (Commercial Source) |
|---|---|
| D-$Trp^6Pro^9$N Et LHRH | Deslorelin |
| [Des-$Gly^{10}$,D-2-Methyl-$Trp^{6,}$, $Pro^9$-NHEt]-LHRH | Avorelin (Metrelin) |
| [D-$Leu^6$, des-Gly-$NH_2{}^{10}$] - LHRH (1–9) NHEt | Leuprolide (Abbott) |
| natural LHRH | |
| D-$trp^6$-LHRH | triptorelin (Debioplarm) (Decapeptyn) |
| [D-Ser ($But^6$des-GLy-$NH_2{}^{10}$] - LHRK (1–9) NHEt | buserelin (Hoechst) |
| Des-$Gly^{10}$-$NH_2$-LH-RH-ethylamide | fertirelin (Takeda) |
| [D-$Trp^6$, $MeLeu^7$, des-Gly-$NH_2{}^{10}$]-LHRH(1–9)NHEt | Lutrelin (Wyeth) |
| [D-Ser($Bu^t$)$^6$, $Azgly^{10}$)--LHRH | Zoladex (Registered Trade Mark)ICI |
| [D--Ser($bu^t$)$^6$,]--LHRH(1–9)NHEt | |
| [D--Lys(Boc)$^6$,des--Gly--$NH_2$10]--LHRH(1–9)NHEt | |
| [D--Glu($OBu^t$)$^6$,des--Gly--$NH_2$10]--LHRH(1–9)NHEt | |
| [D--Asp($OBu^t$)$^6$,des--Gly--$NH_2$10]--LHRH(1–9)NHEt | |
| [D--$Leu^6$Ser($Bu^t$),des--Gly--$NH_2$10]--LHRH(1–9)NHEt | |
| [D--Ser($bu^t$)$^6$,Cys($Bu^t$)$^7$des--Gly--$NH_2$10]--LHRH(1- | |
| [D--Ser($Bu^t$)$^6$,Ser($Bu^t$)$^7$des--Gly--$NH_2$10]--LHRH(1- | |
| [D--$Phe^6$,$Azgly^{10}$]--LHRH | |
| [D--Tyr(Me)$^6$,$Azgly^{10}$]--LHRH | |
| [D--Ser($Bu^t$)$^6$,$Azgly^{10}$]--LHRH | |
| [D--$Tmo^6$]]--LHRH | |

TABLE I-continued

| Agonist structure | Name (Commercial Source) |
|---|---|
| [D--Nal(2)$^6$]--LHRH | |
| [D-His(Benzyl)$^6$,des-glyNH$_2$$^{10}$]-LHRH(1–9)NHEt | historelin |

Preferred GnRH analogs include deslorelin, avorelin, leuprolide, and natural LHRH. Another series of preferred GnRH analogs includes triptorelin, nafarelin, goserelin, buserelin, and fertirelin. Most preferred is deslorelin.

The GnRH analogs are synthezied by any of a variety of conventional techniques. See generally Merrifield, B., Science 232:342 (1986), Norman, A. W. et al., Hormones Academic Press New York 1987. Deslorelin is synthesized by the method of Ajayaghosh, A. et al., J. Org. Chem. 55:2826(1990); Nestor, J. J. et al., Proc. Am. Pept. Symp. 7,109(1981); avorelin by the method of WO 91/18016; leuprolide by the methods of Ger. pat. 2,446,005, U.S. Pat. No. 4,005,063; natural LHRH by the method of Ger. pat. 2,213,737 and Coy et al. Methods Enzymol. 37, 416 (1975); triptorelin by the methods of Ger. patent 2,625,843, U.S. Pat. No. 4,010,125; goserelin by the method of Ger. patent 2,720,245, U.S. Pat. No. 4,100,274; buserelin by the method of Ger. pat. 2,438,352, U.S. Pat. No. 4,024,248; fertirelin by the method of Ger. pat. 2,321,174; U.S. Pat. No. 3,853,837.

III. Solvent

When the composition is used as a LVLCM, it should contain a solvent that the HVLCM is soluble in. Preferably, the substance to be delivered is also soluble in the solvent. The solvent should be non-toxic, water soluble or water miscible, and otherwise biocompatible. Solvents that are toxic should not be used for pharmaceutical or agricultural purposes. The solvents used to inject the composition into animals should not cause significant tissue irritation or necrosis at the site of implantation.

The solvent should be at least water soluble, so that it will diffuse quickly into bodily fluids or other aqueous environment, causing the composition to coagulate or solidify. Examples of suitable solvents include ethanol, ethyl lactate, propylene carbonate, glycofurol, N-methylpyrrolidone, 2 pyrrolidone, propylene glycol, acetone, methyl acetate, ethyl acetate, methyl ethyl ketone, benzyl alcohol, triacetin, dimethylformamide, dimethylsulfoxide, tetrahydrofuran, caprolactam, decylmethylsulfoxide, oleic acid, and 1-dodecylazacycloheptan-2-one. A preferred solvent is ethanol.

When SAIB is used as the HVLCM, the preferred solvents are ethanol, dimethylsulfoxide, ethyl lactate, ethyl acetate, benzyl alcohol, triacetin, N-methylpyrrolidone, propylene carbonate, and glycofurol. SAIB is not miscible with glycerol, corn oil, peanut oil, 1,2-propanediol, polyethylene glycol (PEG200), super refined sesame oil, and super refined peanut oil. Accordingly, the latter group of solvents are not preferred for use with SAIB.

The solvent is typically added to the compositions in an amount in the range from about 5 percent to about 55 percent by weight, relative to the total weight of the composition. Preferably, the solvent is present in the composition in an amount in the range from about 10 percent to about 50 percent by weight. Another preferred range is from about 10 percent to 30 percent by weight.

IV. Veterinary Uses of the LVLCM and HVLCM Compositions

The composition described herein can be administered to the host through a variety of methods which can vary depending on the result to be achieved. When the host is an animal, the composition can be administered, for example, topically, systematically (for example, mucosally (orally, rectally, vaginally, or nasally), or parenterally (intravenously, subcutaneously, intramuscularly, or intraperitoneally) in an appropriate carrier, if desired.

Preferably, for veterinary purposes, the present compositions are administered as solutions or suspensions via injection. When administered via injection as a LVLCM, the small amount of solvent used in the composition leaches into the aqueous fluid of the host, forming a highly viscous depot for the controlled delivery of substances. See, for example, Ansel, H. C. et al., *Pharmaceutical Dosage Forms and Drug Del. Systems*, sixth ed., 1995.

EXAMPLE 1

A. Preparation of SAIB Formulation 1

A solution of deslorelin in DMSO (1.0 wt. %) was prepared. A concentrated solution of 95:5 weight ratio SAIB:DMSO was also prepared. A predetermined amount (2.1870 g) of deslorelin acetate (DA)/DMSO was added to 7.9230 g of the 95:5 SAIB:DMSO solution. The final formulation contained 2.4 mg/mL deslorelin and had an SAIB:DMSO ratio of 75:25.

B. Preparation of SAIB Formulation 2

A solution of deslorelin in ethanol (2.1 wt. %) was prepared. A concentrated solution of 95:5 weight ratio SAIB:ethanol was also prepared. A predetermined amount (1.0376 g) of deslorelin acetate/ethanol was added to 8.9917 g of the 95:5 SAIB:ethanol solution. The final formulation contained 2.3 mg/mL deslorelin and had an SAIB:ethanol ratio of 85:15.

C. Preparation of SAIB Formulation 3

A solution of deslorelin in ethanol (1.9 wt. %) was prepared. A concentrated solution of 95:5 weight ratio SAIB:ethanol was also prepared. A predetermined amount (1.0826 g) of deslorelin acetate/ethanol was added to 7.9085 g of the 95:5 SAIB:ethanol solution. The final formulation contained 2.2 mg/mL deslorelin and had an SAIB:ethanol ratio of 75:25.

D. Preparation of SAIB Formulations 4–8 with 75:25 SAIB:Ethanol for Dose Titration Study A dose titration study was performed using this 75:25 SAIB:ethanol formulation that evaluated deslorelin concentrations of 0.5, 1.0, 1.5, and 2.0 mg/mL. A concentrated solution of SAIB in ethanol (83.6 wt. %) was prepared and sterile filtered using a 0.2 µm hydrophobic filter. Pure ethanol and a solution of deslorelin in ethanol (21.0 mg/g) were sterile filtered using 0.22 µm sterile syringe filters.

Appropriate amounts of sterile SAIB/EtOH and EtOH/Deslorelin solutions were combined with a predetermined amount of sterile ethanol to yield the final mixtures with the desired concentrations. The amounts of each component used and the compositions of the formulations prepared are shown in Table A. The lowest concentration of each formulation produced a solution, while the remaining formulations were suspensions that increased in cloudiness with increasing deslorelin concentration.

TABLE A

Compositions of 75:25 SAIB:Ethanol Formulations for In Vivo Study

| Lot Number | Formula for # | SAIB/EtOH Ratio | DA mg/ml | Amount of Component Added | | |
|---|---|---|---|---|---|---|
| | | | | EtOH | EtOH/Des | SAIB/EtOH |
| X96560 | 4 | 75:25 | 0.5 | 2.49 | 0.74 | 27.91 |
| X96561 | 5 | 75:25 | 1.0 | 1.79 | 1.49 | 28.39 |
| X96562 | 6 | 75:25 | 1.5 | 1.03 | 2.19 | 27.61 |
| X96563 | 7 | 75:25 | 2.0 | 0.31 | 2.91 | 27.64 |
| X96568 | 8 | 75:25 | 0 | 8.74 | — | 77.79 |

E. Preparation of SAIB Formulations 9–12 with 65:35 SAIB:Ethanol for Dose Titration Study.

A dose titration study was also performed using a 65:35 SAIB:ethanol formulation that evaluated deslorelin concentrations of 0.5, 1.0, 1.5, and 2.0 mg/mL. A concentrated solution of SAIB in ethanol (83.6 wt. %) was prepared and sterile filtered using a 0.2 μm hydrophobic filter. Pure ethanol and a solution of deslorelin in ethanol (21.0 mg/g) were sterile filtered using 0.22 μm sterile syringe filters.

Appropriate amounts of sterile SAIB/EtOH and EtOH/Deslorelin solutions were combined with a predetermined amount of sterile ethanol to yield the final mixtures with the desired concentrations. The amounts of each component used and the compositions of the formulations prepared are shown in Table B. The lowest concentration of each formulation produced a solution, while the remaining formulations were suspensions that increased in cloudiness with increasing deslorelin concentration.

TABLE B

Compositions of 65:35 SAIB:Ethanol Formulations for In Vivo Study

| Lot Number | Formula for # | SAIB/EtOH Ratio | DA mg/ml | Amount of Component Added | | |
|---|---|---|---|---|---|---|
| | | | | EtOH | EtOH/Des | SAIB/EtOH |
| X96564 | 9 | 65:35 | 0.5 | 5.56 | 0.74 | 23.23 |
| X96565 | 10 | 65:35 | 1.0 | 4.98 | 1.43 | 22.29 |
| X96566 | 11 | 65:35 | 1.5 | 447 | 2.22 | 23.18 |
| X96567 | 12 | 65:35 | 2.0 | 3.64 | 2.17 | 22.60 |

EXAMPLE 2

Mares used in this experiment were from the resident herd at the LSU Agricultural Center Horse Farm and were all of light horse type, mainly Quarter Horses, Thoroughbreds and Arabians. All mares were in good body condition and were maintained on native summer grass pasture (predominantly bermudagrass). The majority of mares in the herd were not bred the previous season, whereas six had foaled within 30 days and were lactating. The mares were placed on a daily regimen of estrous detection beginning June 1, and were all administered a general health and reproductive soundness exam during June. Only mares with good health, satisfactory vulvar and vaginal conformations, and apparently normal uterine and ovarian conformations were placed into a pool of potential candidates for treatment. Most of the mares were between 11 and 14 years of age (range: 8 to 22 years) and weighed 400 to 650 kg.

In this study, three experimental formulations were prepared by weighing and mixing SAIB (SABER, SBS Inc., Birmingham, Ala.), diluting solvent and Deslorelin added to give a final concentration of 2.1 mg/ml. SAIB: diluting solvent compositions were: 75:25 w/w SAIB:DMSO in Formulation 1 (see example 1A); 85:15 w/w SAIB:Ethanol in Formulation 2 (see example 1B); and 75:25 w/w SAIB:Ethanol in Formulation 3 (see example 1C). Resultant experimental formulations were hydrophobic low viscosity after i.m. injection as the solvent diffused, leaving behind a SAIB-DA matrix that released DA by diffusion through the highly viscous SAIB, accompanied by degradation of SAIB to sucrose and its corresponding aliphatic acids from which the sucrose ester was prepared. In addition, a negative control (1 mL of 0.9% NaCl USP, injected i.m.) was prepared. As mares entered estrus after July 1, their ovaries were evaluated daily by transrectal ultrasonography to assess follicular sizes and uterine appearance. Once a mare met the following two criteria, she was assigned to treatment based on a predetermined random allotment: 1) she had to be in estrus, and 2) she had to have a follicle of at least 30 mm in diameter, but not more than 40 mm diameter. Ultrasound evaluations were performed each morning, and mares were normally treated before noon. To avoid any possible biases in the data, the personnel administering treatments were different from those assessing follicular and estrous characteristics and injection sites. In addition, the three SABER formulations were color coded and their actual contents were unknown to all farm personnel.

Once a mare was treated, her ovaries were assessed via ultrasonography every 12 h until she ovulated. Sizes of the measurable follicles on each ovary were recorded, and ovulation was determined by various changes in size, softness, and the appearance of the dominant follicle as described in detail by Ginther (Ginther, O. J. *Ultrasonic Imaging and Reproductive Events in the Mare* Equiservices Cross Plains, Wis. 1986) In addition, blood samples were collected at 24 h before treatment-(−24 h); immediately before treatment (time 0); at 1, 3, 6, 12, 24, 36, and 48 h after treatment; and then every 24 h until 24 h after ovulation for measurement of progesterone and(or) luteinizing hormone (LH) concentrations. These blood samples were drawn via jugular venipuncture into heparinized, evacuated tubes, and the tubes were placed at 5° C. until plasma was harvested by centrifugation. Progesterone was measured by radioimmunoassay with commercially available reagents (Diagnostic Systems Laboratories, Inc., Webster, Tex.) and LH was measured by radioimmunoassay as described by Thompson et al. 1983. J. Anim. Sci. 56:678–686.

Each day after treatment for 7 days, the injection site of each mare was assessed for three characteristics: 1) swelling, which was scored as 0=none, 1=slight (1 cm diameter or less), 2=slight (1 to 2.5 cm diameter), and 3=significant (greater than 3 cm diameter); 2) sensitivity to touch, which was scored as yes or no; and 3) skin temperature elevation, which was also scored as yes or no. Deslorelin concentrations were determined in the blood samples collected at −24, 0, 1, 3, 6, 12, 24, 36, 48 and 72 h relative to treatment. Immediately after the sample was withdrawn from the jugular vein, a 1 -mL aliquot was removed and added to 4 mL of acetone in a 12×75 mm disposable glass tube. This mixture was inverted several times and capped for storage at −15° C. At a later date, the extracts were centrifuged and the acetone decanted into a second tube. The acetone was then dried under a stream of air, and the residual aqueous solution was diluted back to 1.0 mL with assay buffer. Deslorelin was measured in the extracts by radioimmunoassay using an anti-GnRH antiserum (Rabb et al., 1990. J. Anim. Sci. 68:3322–3329) and radioiodinated Deslorelin. The Deslorelin was radioiodinated by the chloramine-T method and isolated by QAE-Sephadex chromatography as described for GnRH by Nett et al., Endocrinology 101:1135 (1977). Because endogenous GnRH is not present in sufficient quantities in jugular blood for detection, any immunoreactivity in the samples was assumed to be Deslorelin and not GnRH.

During the course of the experiment, one mare exhibited an unusually long estrous period and did not ovulate until 216 h after treatment. Because her response was so different from all other mares, her ovulation time was compared to the remaining mares receiving Deslorelin and was found to be 3.82 standard deviations away from their average (P<0.01). Thus, the data from this mare were removed from all analyses, and an additional mare was treated with the slow release formulation (see example 1A) to take her place.

Data for single time points were analyzed by one-way analysis of variance using the General Linear Models procedure of SAS. 1988. SAS/STAT® User's Guide (Release 6.03). SAS Inst. Inc., Cary, N.C. For each variable, the comparison between the saline treated mares and all mares receiving Deslorelin was included in the analysis, as well as individual comparisons between each group receiving Deslorelin and the saline group; these comparisons were based on the LSD value calculated from the pooled error variance. For percentage of mares ovulating within 48 h, mares were scored either 1 (yes) or 0 (no) and a one-way analysis of variance was performed on those data rather than using the Chi-square method. Data from repeated sampling (e.g., LH concentrations) were analyzed by split-plot analysis of variance in which the effect of treatment was tested with the horse (treatment) term, and the treatment×time interaction was tested with the residual error variance. Net areas under the response curves were also calculated for Deslorelin concentrations from 0 to 24 h after treatment, and for LH concentrations from 0 to 48 h after treatment; these areas were analyzed by one-way analysis of variance as described above.

Ovulation was confirmed by Ultrasound (US) and elevated progesterone ($P_4$) levels. End points studied included hours to ovulation, percentage (%) of mares ovulating within 48 h and LH, $P_4$ and DA levels measured by RIA's. In addition, injection site swelling scores (0 to 3; 0=none, 1=slight, 2=moderate, 3=significant), injection site sensitivity (Yes/No) and temperature elevation at the injection site (Yes/No) were also studied.

Results showed that plasma DA (Deslorelin acetate) concentrations were significantly increased after treatment in all three SAIB formulations with peak levels of 1902 to 1699 pg/ml. Area under the response curve (AUC) for the first 24 hours after injection also confirmed significant increase in SAIB treated mares compared to saline treated controls (See Table II).

In Table II, a significant increase in the % of mares ovulating within 48 h (when compared with saline) was detected in mares given formulations 2 and 3.

TABLE II

Mare Efficacy & Hormonal Data

|  | Hours to Ovulation | | Ovulation | DA AUC |
|---|---|---|---|---|
|  | (US) | ($P_4$) | by 48 h | First 24 h |
| Saline Controls | 102 | 99 | 0% | 148.68 |
| Formulation 1 (example 1A) | 81 | 72 | 50% | 4983.20[1] |
| Formulation 2 (1B) | 69 | 51[2] | 75[2]% | 6026.19[1] |
| Formulation 3 (1C) | 48[3] | 48[1] | 100[1]% | 6037.52[1] |

Safety - Injection Site (IS) Data

|  | Swelling Score (0–3) on Days | | | | Sensitive at IS (%) | Temp. Elevation at IS (%) |
|---|---|---|---|---|---|---|
|  | 1 | 3 | 5 | 7 | | |
| Saline Controls | 0 | 0 | 0 | 0 | 0% | 0% |
| Formulation 1 (example 1A) | .25 | 0 | 0 | 0 | 0% | 0% |
| Formulation 2 (1B) | .5 | .25 | .25 | 0 | 0% | 0% |
| Formulation 3 (1C) | .5 | 0 | 0 | 0 | 0% | 0% |

($P < .01$)[1]; ($P < .05$)[2]; ($P < .07$)[3]

There was no effect of treatment (P=0.467) nor any interaction with time (P=0.817) for swelling scores at the injection site, nor was there any sensitivity or elevation of skin temperature at the injection site for any treatment.

AUC for LH in the first 48 h, indicated that mares receiving Formulation 3 (P=0.01) and Formulation 2 (P=0.1) were increased compared to the saline treated mares. In addition, plasma LH concentration increased immediately (P<0.0003) in all treatments except saline, peaked at 6 h after injection and remained elevated through 36 to 48 h after treatment as shown in FIG. 1.

The results demonstrate that Formulations 2 and 3 effectively released Deslorelin which stimulated ovulatory levels of LH and hastened ovulation in mares with 7 of 8 mares ovulating within 48 hours after treatment. Furthermore, the data inicate that all 3 SAIB formulations exhibited excellent biocompatibility as judged by minimal injection site reactions which were similar to controls.

EXAMPLE 3

Ninety cyclic mares of various light horse breeds, 3 to 16 years old and weighing 400 to 650 kg were used. Mares were randomly assigned to one of 9 blinded color groups (n=10/group) to avoid interpretation bias. Treatments were 2 experimental formulation groups containing: 0.5, 1.0, 1.5 or 2.0 mg Deslorelin acetate (DA) designed to deliver DA at differing rates for approximately 12 to 36 hours (h) after a 1 ml intramuscular (i.m.) injection using a 21 gauge needle; and a negative control consisting of SAIB containing no drug which was also administered as a 1 ml i.m. injection.

Experimental formulations were prepared by weighing and mixing SAIB (SABER, SBS Inc., Birmingham, Ala.), diluting solvent and DA added to give the appropriate final concentration of 0.5, 1.0, 1.5 or 2.0 mg/ml. SAIB:diluting solvent compositions were: 75:25 w/w SAIB:Ethanol in Formulations 4–8 (see example 1D) and 65:35 w/w SAIB:Ethanol in Formulations 9–12 (see example 1E).

Estrus mares' ovaries were examined daily by ultrasound (US) and were treated once a follicle between 30 mm and 40 mm was detected. Thereafter, mares' ovaries were examined every 24 h until ovulation which was confirmed by US.

The two major efficacy variables in the study were (a) interval in hours from treatment to ovulation, and (b) the percent of mares ovulating within 48 hours of treatment. The former was statistically analyzed using SAS® Cox's regression model (proportional hazards). The later was statistically analyzed using logistic regression investigating the effects of formulation and dose. The major safety variables in the study were (a) visible signs of swelling scores (b) sensitivity to touch, and (c) skin temperature elevation at the injection site. These variables were to be statistically analyzed by repeated measures analysis for categorical data using SAS PROC CATMOD, however, because no swelling, sensitivity or temperature elevations were detected the analysis was not performed.

Ovulation data are presented in Table III. Using the Cox model (linear) in doses for both formulation groups, the coefficient for the 75:25 SAIB/Ethanol formulation was highly significant (p<0.01 using a two sided test), but the coefficient for 65:35 SAIB/Ethanol formulations were not significant indicating the superiority of the 75:25 SAIB/Ethanol formulations (see example 1C).

TABLE III

Mare Ovulation Data

Control SAIB Formulation

| TREATMENTS | Hours to Ovulation | Mares Ovulating by 48 hours (%) |
|---|---|---|
| Negative Control (0 mg) | 112.8 | 20% (34%; 37%) |

75:25 SAIB/Ethanol Formulation

| TREATMENTS Example 1D | Hours to Ovulation | Mares Ovulating by 48 hours (%) |
|---|---|---|
| Formulation 4 (0.5 mg) | 88.8 | 30% (54%; 52%) |
| Formulation 5 (1.0 mg) | 50.4 | 90% (74%; 70%) |
| Formulation 6 (1.5 mg) | 55.2 | 80% (90%; 84%) |
| Formulation 7 (2.0 mg) | 50.4 | 90% (98%; 92%) |

65:35 SAIB/Ethanol Formulation

| TREATMENTS Example 1E | Hours to Ovulation | Mares Ovulating by 48 hours (%) |
|---|---|---|
| Formulation 9 (0.5 mg) | 60 | 70%* (38%; 41%) |
| Formulation 10 (1.0 mg) | 74.4 | 50%* (40%; 48%) |
| Formulation 11 (1.5 mg) | 110.4 | 50%* (42%; 56%) |
| Formulation 12 (2.0 mg) | 79.2 | 60%* (54; 44%) |

*Actual % (Cox's proportional hazards model-linear predicted %; logistics model predicted %) at (p < 0.01)

Using the logistic model (linear) in doses for both formulations, the effect of the 75:25 SAIB/ethanol formulations were also highly significant (p,0.01 using a two sided test), whereas the effect of the 65:35 SAIB/ethanol formulations were highly significant (p<0.1 using a two sided test). Moreover, the slope for the 75:25 formulations was significantly greater than that for the 65:35 formulations (β) (p=0.026) indicating the superiority of the 75:25 formulations.

Quadratic terms were not significant for either analysis indicating that the linear models used provided a sufficient representation for all nine groups. Predicted percentage of mares ovulating by 48 hours using both types of analysis are presented in table III in parenthesis next to the actual observed data.

The major safety variables in the study were visible signs of swelling, sensitivity to touch and skin temperature elevation at the injection site all of which were undetectable in the 90 mares studied. The absence of any observed swelling, sensitivity or elevation of skin temperature at the injection site of any of the treatments strongly suggest excellent biocompatiblility of the present SAIB formulation when produced using filter sterilization and administered using smaller 21 gauge needles (See Table IV).

TABLE IV

Mare Safety - Injection Site (IS) Data

| TREATMENTS | Swelling Score (0–3) on Days | | | | Sensitivity at IS (%) | Temp. Elevation at IS (%) |
|---|---|---|---|---|---|---|
| Examples 1D & 1E | 1 | 3 | 5 | 7 | | |
| Negative Control (0 | 0 | 0 | 0 | 0 | 0% | 0% |
| Formulation 4 (0.5 mg) | 0 | 0 | 0 | 0 | 0% | 0% |
| Formulation 5 (1.0 mg) | 0 | 0 | 0 | 0 | 0% | 0% |
| Formulation 6 (1.5 mg) | 0 | 0 | 0 | 0 | 0% | 0% |
| Formulation 7 (2.0 mg) | 0 | 0 | 0 | 0 | 0% | 0% |
| Formulation 9 (0.5 mg) | 0 | 0 | 0 | 0 | 0% | 0% |
| Formulation 10 (1.0 | 0 | 0 | 0 | 0 | 0% | 0% |
| Formulation 11 (1.5 | 0 | 0 | 0 | 0 | 0% | 0% |
| Formulation 12 (2.0 | 0 | 0 | 0 | 0 | 0% | 0% |

This study clearly demonstrated the superiority of the 75:25 SAIB/ethanol formulation compared to the 65:35 SAIB/ethanol formulation for advancing ovulation. Furthermore, both Cox's proportional hazard and logistic modeling predicted a positive response rate for stimulating ovulation by 48 hours of greater than 70% for the 1 mg dose, 80% for the 1.5 mg dose and greater than 90% for the 2 mg dose of DA, indicating that such treatments effectively stimulate ovulatory levels of LH and hasten ovulation in the mare. Lastly, the safety data indicate that all nine SAIB formulations exhibited excellent biocompatibilty as judged by no detectable injection site reactions.

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:

1. A composition for the controlled release of GnRH or analogs thereof in mares to induce ovulation, comprising:
    (a) a non-polymeric, non-water soluble liquid carrier material having a viscosity of at least 5,000 cP at 37° C. that does not crystallize neat under ambient or physiological conditions;
    (b) GnRH or analogs, or combination thereof.

2. The composition of claim 1, wherein the non-water soluble liquid carrier material is sucrose acetate isobutyrate.

3. The composition of claim 2, wherein the non-water soluble liquid carrier material is present in an amount from about 99.5 percent to about 10 percent by weight, relative to the total weight of the composition.

4. The composition of claim 3, wherein the non-water soluble liquid carrier material is present in an amount from about 95 percent to about 25 percent by weight, relative to the total weight of the composition.

5. The composition of claim 2, wherein the composition further comprises a solvent in which the non-water soluble liquid carrier is soluble.

6. The composition of claim 5, wherein the solvent is selected from the group consisting of ethanol, dimethylsulfoxide, ethyl lactate, ethyl acetate, benzyl alcohol, triacetin, N-methylpyrrolidone, propylene carbonate, and glycofurol.

7. The composition of claim 6, wherein the solvent is ethanol.

8. The composition of claim 5, wherein the solvent is present in an amount from about 10 to about 50 percent by weight, relative to the weight of the composition.

9. The composition of claim 1, wherein the analog is deslorelin.

10. The composition of claim 1, wherein the analog is selected from deslorelin, avorelin, leuprolide, and natural LHRH.

11. A liquid composition for the controlled release of GnRH or analogs thereof in mares to induce ovulation, comprising sucrose acetate isobutyrate and ethanol in a weight ratio of between about 75:25 and about 60:40, and GnRH or analog thereof or combination thereof in a concentration of between about 0.1 to about 5.0 mg/ml of liquid composition, to provide a dose of between about 0.3 mg and about 10 mg of GnRH or analog thereof or combination thereof.

12. A liquid composition for the controlled release of GnRH or analogs thereof in mares to induce ovulation, comprising sucrose acetate isobutyrate and ethanol in a weight ratio of between about 75:25 and about 60:40, and GnRH or analog thereof or combination thereof in a concentration of between about 1.0 to about 2.5 mg/ml of liquid composition, to deliver a dose of between about 0.3 mg and about 10 mg of GnRH or analog thereof or combination thereof.

13. The liquid composition of claim 11, wherein the analog of GnRH is Deslorelin.

14. The liquid composition of claim 12, wherein the analog of GnRH is Deslorelin.

15. The liquid composition of claim 11, said composition sterilized before administration to mares.

16. The liquid composition of claim 12, said composition sterilized before administration to mares.

17. The liquid composition of any of claim 11, said composition filter sterilized before administration to mares.

18. The liquid composition of any of claim 12, said composition filter sterilized before administration to mares.

19. A filter sterilized liquid composition for the controlled release of Deslorelin in mares to induce ovulation, comprising sucrose acetate isobutyrate and ethanol in a weight to weight ratio of about 75:25, and Deslorelin at a concentration of between about 0.1 and about 5.0 mg/ml of liquid composition, to deliver a dose between about 1 mg and about 2 mg of deslorelin, said composition administrable by injection.

20. A filter sterilized liquid composition for the controlled release of Deslorelin in mares to induce ovulation, comprising sucrose acetate isobutyrate and ethanol in a weight to weight ratio of about 75:25, and Deslorelin at a concentration of between about 1.0 and about 2.5 mg/ml of liquid composition, to deliver a dose between about 1 mg and about 2 mg of deslorelin, said composition administrable by injection.

* * * * *

UNITED STATES PATENT AND TRADEMARK OFFICE
CERTIFICATE OF CORRECTION

PATENT NO. : 6,051,558  
DATED : April 18, 2000  
INVENTOR(S) : Burns et al.

Page 1 of 1

It is certified that error appears in the above-identified patent and that said Letters Patent is hereby corrected as shown below:

<u>Column 3,</u>  
Lines 16-17, please delete:  
"composition adminstratable by injection. ps I. High Viscosity Liquid Carrier Material (HVLCM)"  
and insert:  
-- composition administratable by injection.  
I. High Viscosity Liquid Carrier Material (HVLCM) --

Signed and Sealed this

Tenth Day of May, 2005

JON W. DUDAS  
*Director of the United States Patent and Trademark Office*